(12) United States Patent
Mistry

(10) Patent No.: US 10,456,262 B2
(45) Date of Patent: Oct. 29, 2019

(54) PATIENT-SPECIFIC IMPLANT FLANGES WITH BONE SIDE POROUS RIDGES

(71) Applicant: Howmedica Osteonics Corp., Mahwah, NJ (US)

(72) Inventor: Amit Mistry, Weston, FL (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 15/664,254

(22) Filed: Jul. 31, 2017

(65) Prior Publication Data
US 2018/0036129 A1    Feb. 8, 2018

Related U.S. Application Data

(60) Provisional application No. 62/369,829, filed on Aug. 2, 2016.

(51) Int. Cl.
*A61F 2/34* (2006.01)
*A61F 2/30* (2006.01)

(52) U.S. Cl.
CPC ............ *A61F 2/34* (2013.01); *A61F 2/30734* (2013.01); *A61F 2/30942* (2013.01);
(Continued)

(58) Field of Classification Search
CPC ........ A61F 2002/343; A61F 2002/3432; A61F 2/34; A61F 2002/30578; A61F 2/30734; A61F 2002/30736; A61F 2002/30576; A61F 2002/30879; A61F 2002/30774; A61F 2002/30777; A61F 2002/30779; A61F 2002/30784; A61F 2002/30794; A61F 2002/30818; A61F 2002/3425;
(Continued)

(56) References Cited

U.S. PATENT DOCUMENTS 2,947,308 A    8/1960 Gorman
3,806,960 A    4/1974 Weber
(Continued)

FOREIGN PATENT DOCUMENTS

DE    19815329 A1    10/1999
GB    2476319 A    6/2011
(Continued)

OTHER PUBLICATIONS

Extended European Search Report for Application No. EP17184362.6 dated Oct. 23, 2017.
(Continued)

*Primary Examiner* — David H Willse
*Assistant Examiner* — Javier G Blanco
(74) *Attorney, Agent, or Firm* — Lerner, David, Littenberg, Krumholz & Mentlik, LLP

(57) ABSTRACT

An implant includes a base, a flange, and ridge. The flange extends from the base. The ridge extends from the flange. A hole extends through the flange and the ridge. A system with the implant includes a fastener extending through the ridge of the implant. The implant is placed into bone by securing a base of the implant to a main complementary contact surface of bone and by securing a ridge extending outwardly from a flange of the implant to a secondary complementary contact surface of bone spaced from the main complementary contact surface.

18 Claims, 8 Drawing Sheets

(52) U.S. Cl.
CPC ........... *A61F 2002/3092* (2013.01); *A61F 2002/3096* (2013.01); *A61F 2002/30578* (2013.01); *A61F 2002/30736* (2013.01); *A61F 2002/30774* (2013.01); *A61F 2002/30777* (2013.01); *A61F 2002/30784* (2013.01); *A61F 2002/30828* (2013.01); *A61F 2002/30879* (2013.01); *A61F 2002/30945* (2013.01); *A61F 2002/30962* (2013.01); *A61F 2002/3401* (2013.01); *A61F 2002/343* (2013.01); *A61F 2002/3403* (2013.01); *A61F 2002/3404* (2013.01); *A61F 2002/3408* (2013.01); *A61F 2002/3432* (2013.01); *A61F 2002/3483* (2013.01)

(58) Field of Classification Search
CPC ..... A61F 2002/3427; A61F 2002/3401; A61B 17/8066
See application file for complete search history.

(56) References Cited

U.S. PATENT DOCUMENTS

| | | | |
|---|---|---|---|
| 3,874,003 A | 4/1975 | Moser et al. |
| 3,903,549 A | 9/1975 | Deyerle |
| 4,101,985 A | 7/1978 | Baumann et al. |
| 4,450,592 A | 5/1984 | Niederer et al. |
| 4,502,161 A | 3/1985 | Wall |
| 4,681,589 A | 7/1987 | Tronzo |
| 4,743,262 A | 5/1988 | Tronzo |
| 4,813,960 A | 3/1989 | Muller |
| 4,904,265 A | 2/1990 | MacCollum et al. |
| 4,919,675 A | 4/1990 | Dietschi |
| 5,156,625 A | 10/1992 | Marchetti et al. |
| 5,176,711 A | 1/1993 | Grimes |
| 5,192,329 A | 3/1993 | Christie et al. |
| 5,290,315 A | 3/1994 | DeCarlo, Jr. |
| 5,314,488 A | 5/1994 | Hayashi et al. |
| 5,370,704 A | 12/1994 | DeCarlo, Jr. |
| 5,425,778 A | 6/1995 | Zichner et al. |
| 5,549,691 A | 8/1996 | Harwin |
| 5,549,692 A | 8/1996 | Hauser et al. |
| 5,609,646 A | 3/1997 | Field et al. |
| 5,702,477 A | 12/1997 | Capello et al. |
| 5,716,412 A | 2/1998 | DeCarlo, Jr. et al. |
| 5,725,593 A | 3/1998 | Caracciolo |
| 5,824,107 A | 10/1998 | Tschirren |
| 5,871,548 A | 2/1999 | Sanders et al. |
| 5,928,288 A | 7/1999 | Wilson |
| 5,931,870 A | 8/1999 | Cuckler et al. |
| 6,004,353 A | 12/1999 | Masini |
| 6,059,830 A | 5/2000 | Lippincott, III et al. |
| 6,059,833 A | 5/2000 | Doets |
| 6,132,674 A | 10/2000 | Compton et al. |
| 6,136,034 A | 10/2000 | Townley |
| 6,162,257 A | 12/2000 | Gustilo et al. |
| 6,299,647 B1 | 10/2001 | Townley |
| 6,306,173 B1 | 10/2001 | Masini |
| 6,402,787 B1 | 6/2002 | Pope et al. |
| 6,416,553 B1 | 7/2002 | White et al. |
| 6,454,809 B1 | 9/2002 | Tornier |
| 6,458,161 B1 | 10/2002 | Gibbs et al. |
| 6,503,281 B1 | 1/2003 | Mallory |
| 6,537,321 B1 | 3/2003 | Horber |
| 6,682,567 B1 | 1/2004 | Schroeder |
| 6,709,462 B2 | 3/2004 | Hanssen |
| 6,797,007 B1 | 9/2004 | Von Chamier et al. |
| 6,811,569 B1 | 11/2004 | Afriat et al. |
| 6,827,742 B2 | 12/2004 | Hayes, Jr. et al. |
| 6,896,703 B2 | 5/2005 | Barbieri et al. |
| 6,908,486 B2 | 6/2005 | Lewallen |
| 7,252,684 B2 | 8/2007 | Dearnaley |
| 7,291,177 B2 | 11/2007 | Gibbs |
| 7,485,148 B2 | 2/2009 | Wozencroft et al. |
| 7,537,664 B2 | 5/2009 | O'Neill et al. |
| 7,584,080 B2 | 9/2009 | Taylor et al. |
| 7,597,715 B2 | 10/2009 | Brown et al. |
| 7,604,667 B2 | 10/2009 | DeSmet et al. |
| 7,641,656 B2 * | 1/2010 | Collins .............. A61B 17/1655 606/79 |
| 7,682,399 B2 | 3/2010 | Shields et al. |
| 7,713,306 B2 | 5/2010 | Gibbs |
| 7,879,275 B2 | 2/2011 | Smith et al. |
| 7,883,653 B2 | 2/2011 | Smith et al. |
| 7,918,896 B2 | 4/2011 | DeSmet et al. |
| 7,985,260 B2 | 7/2011 | Keefer et al. |
| 7,993,408 B2 | 8/2011 | Meridew et al. |
| 8,010,180 B2 | 8/2011 | Quaid et al. |
| 8,021,432 B2 | 9/2011 | Meridew et al. |
| 8,066,778 B2 | 11/2011 | Meridew et al. |
| 8,123,814 B2 | 2/2012 | Meridew et al. |
| 8,123,816 B2 | 2/2012 | Shields et al. |
| 8,197,550 B2 | 6/2012 | Brown et al. |
| 8,211,182 B2 | 7/2012 | Linares |
| 8,211,184 B2 | 7/2012 | Ries et al. |
| 8,328,875 B2 | 12/2012 | Linares |
| 8,409,294 B2 | 4/2013 | Divoux |
| 8,454,705 B2 | 6/2013 | Pressacco et al. |
| 8,506,644 B1 | 8/2013 | Ho Ba Tho et al. |
| 8,535,384 B2 | 9/2013 | Davenport et al. |
| 8,551,181 B2 | 10/2013 | Meridew et al. |
| 8,556,901 B2 | 10/2013 | Anthony et al. |
| 8,574,306 B2 | 11/2013 | Ries et al. |
| 8,597,361 B2 | 12/2013 | Sidebotham et al. |
| 8,597,365 B2 | 12/2013 | Meridew |
| 8,700,198 B2 | 4/2014 | Conway et al. |
| 8,728,387 B2 | 5/2014 | Jones et al. |
| 8,764,843 B2 | 7/2014 | Gradel |
| 8,808,390 B2 | 8/2014 | Lewis et al. |
| 8,845,748 B2 | 9/2014 | Gradel |
| 8,858,558 B2 | 10/2014 | Linares |
| 8,979,926 B2 | 3/2015 | Quinn et al. |
| 8,998,909 B2 | 4/2015 | Gillman et al. |
| 9,017,416 B2 | 4/2015 | McMinn |
| 9,023,112 B2 | 5/2015 | Komistek |
| 9,089,430 B2 | 7/2015 | Pappas et al. |
| 9,125,753 B2 | 9/2015 | Caballes |
| 9,161,760 B2 | 10/2015 | Suarez et al. |
| 9,168,143 B2 | 10/2015 | Gradel |
| 9,180,010 B2 | 11/2015 | Dong et al. |
| 9,192,478 B2 | 11/2015 | Weeden |
| 9,275,192 B2 | 3/2016 | Kang et al. |
| 2003/0153982 A1 | 8/2003 | Pria |
| 2004/0093090 A1 | 5/2004 | Barbieri et al. |
| 2005/0288793 A1 | 12/2005 | Dong et al. |
| 2006/0009857 A1 | 1/2006 | Gibbs et al. |
| 2006/0116774 A1 | 6/2006 | Jones et al. |
| 2006/0147332 A1 | 7/2006 | Jones et al. |
| 2006/0190089 A1 | 8/2006 | Montoya et al. |
| 2006/0217720 A1 | 9/2006 | Chieng |
| 2006/0217815 A1 | 9/2006 | Gibbs et al. |
| 2006/0241781 A1 | 10/2006 | Brown et al. |
| 2007/0129809 A1 | 6/2007 | Meridew et al. |
| 2007/0173948 A1 | 7/2007 | Meridew et al. |
| 2009/0240256 A1 | 9/2009 | Smith |
| 2010/0004754 A1 | 1/2010 | Brown et al. |
| 2010/0049329 A1 | 2/2010 | Vio et al. |
| 2010/0063597 A1 | 3/2010 | Gradel |
| 2010/0262257 A1 | 10/2010 | Cruchet |
| 2010/0306987 A1 | 12/2010 | Gradel |
| 2011/0014081 A1 | 1/2011 | Jones et al. |
| 2011/0054628 A1 | 3/2011 | Banks et al. |
| 2011/0194739 A1 | 8/2011 | Vincent et al. |
| 2012/0016486 A1 | 1/2012 | Yokoo |
| 2012/0016487 A1 | 1/2012 | Conway et al. |
| 2012/0022662 A1 * | 1/2012 | Conway .............. A61B 17/8066 623/22.21 |
| 2012/0053590 A1 * | 3/2012 | Allen ................ A61B 17/1746 606/87 |
| 2012/0083895 A1 | 4/2012 | Conway et al. |
| 2012/0089235 A1 | 4/2012 | Conway et al. |
| 2012/0109137 A1 | 5/2012 | Iannotti et al. |
| 2012/0109150 A1 | 5/2012 | Quaid et al. |
| 2012/0123553 A1 | 5/2012 | Sidebotham et al. |

(56) References Cited

U.S. PATENT DOCUMENTS

| | | |
|---|---|---|
| 2012/0130503 A1 | 5/2012 | Forsell |
| 2012/0179270 A1 | 7/2012 | Nevins et al. |
| 2012/0245702 A1 | 9/2012 | Pappas et al. |
| 2012/0289965 A1 | 11/2012 | Gelaude et al. |
| 2013/0035766 A1 | 2/2013 | Meridew |
| 2013/0046389 A1 | 2/2013 | Fierlbeck et al. |
| 2013/0053968 A1 | 2/2013 | Nardini et al. |
| 2013/0199259 A1 | 8/2013 | Smith |
| 2013/0268085 A1* | 10/2013 | Dong ............ A61F 2/28 623/23.5 |
| 2014/0039638 A1 | 2/2014 | Meridew et al. |
| 2014/0088724 A1 | 3/2014 | Meridew |
| 2014/0131924 A1 | 5/2014 | McMinn |
| 2014/0135940 A1 | 5/2014 | Goldstein et al. |
| 2014/0180296 A1 | 6/2014 | Gillman et al. |
| 2014/0180430 A1 | 6/2014 | Gillman et al. |
| 2014/0180431 A1 | 6/2014 | Conway et al. |
| 2014/0364958 A1 | 12/2014 | Gradel |
| 2015/0105861 A1 | 4/2015 | Gunther et al. |
| 2015/0112443 A1 | 4/2015 | Gelaude |
| 2015/0335444 A1 | 11/2015 | Caballes |

FOREIGN PATENT DOCUMENTS

| | | |
|---|---|---|
| JP | 2014144162 A | 8/2014 |
| WO | 2008146141 A2 | 12/2008 |
| WO | 2009115196 A1 | 9/2009 |
| WO | 2011012892 A1 | 2/2011 |
| WO | 2011080260 A1 | 7/2011 |
| WO | 2011156504 A2 | 12/2011 |
| WO | 2011156508 A2 | 12/2011 |
| WO | 2012141788 A1 | 10/2012 |
| WO | 2012141790 A1 | 10/2012 |
| WO | 2012172293 A2 | 12/2012 |
| WO | 2013170872 A1 | 11/2013 |
| WO | 2014099450 A1 | 6/2014 |

OTHER PUBLICATIONS

Examination Report for Australian Application No. 2017210513 dated Dec. 18, 2017.

* cited by examiner

PATIENT-SPECIFIC IMPLANT FLANGES WITH BONE SIDE POROUS RIDGES

CROSS-REFERENCE TO RELATED APPLICATION

The present application claims the benefit of the filing date of U.S. Provisional Patent Application No. 62/369,829 filed Aug. 2, 2016, the disclosure of which is hereby incorporated herein by reference.

FIELD OF THE INVENTION

The present invention relates generally to procedures and implants to treat joint failure, and in particular relates to customized implants for surgical revision procedures.

BACKGROUND OF THE INVENTION

Over time, artificial joints, in particular hip joints, become damaged due to normal wear and tear of any one or any combination of the prosthetic implant, the bone interfacing with the implant, the bone surrounding the implant, and in more extreme cases, due to infection of the surrounding bone. In light of the damage, the prosthesis does not fit the bone securely and is ineffective in providing appropriate support and movement for a patient, often causing the patient pain. To repair such defects in the case of damaged hip joints, a surgeon manually fits a revision system, such as the Restoration® GAP II Revision Acetabular System which includes flanges extending from a central dome, i.e., acetabular cup device, to the patient's acetabulum. During such manual procedures, the surgeon has to use specialized tools to manually bend and trim substantially rigid flanges of the implant to desired shapes that conform to the patient's pelvic bone, in particular the ilium. The surgeon then secures both the central dome and flanges to the pelvic bone using bone screws placed through screw holes having a standardized configuration. Such manual techniques potentially expose the patient to a lack of conformity between the implant and the bone that can lead to loosening of the implant or material debridement caused by movement of the implant due to undesired play between the implant and the bone.

Additionally, implants for these revision systems are provided in a limited number of standard shapes and sizes that may not conform all that closely to a patient's anatomy or that may not have flanges that align with more dense regions of bone for fastening using the bone screws. These limitations create a higher tendency for future damage or failure earlier than anticipated. To compensate for these issues, porous augments and shim augments have been attached to both the central dome as well as to the flanges to provide regions for bone ingrowth. However, the use of augments requires components additional to the main implant and, like the main implant, such augments are substantially inflexible and have screw holes in a standardized configuration that match the screw holes of the portion of the main implant underlying the augments.

In light of the limitations of revision implants, there exists a need for an implant that more closely conforms to and integrates with interfacing bone.

SUMMARY OF THE INVENTION

In accordance with an aspect, an implant may include a base, one or more flanges extending from the base, and one or more ridges extending from each flange. The implant may include opposing convex and concave base surfaces. The convex base surface of the implant may be configured for placement against bone. In some arrangements, the concave base surface may define a surface for receipt of an insert which may include a bearing, preferably a polyethylene or other polymeric bearing, for receipt of another bone or a prosthesis that replaces the other bone. In alternative arrangements, the concave base surface may define a bearing surface for receipt of such bone or prosthesis that replaces the other bone. The quantity, location, orientation, and shape of the flanges and the ridges may be patient-specific. The ridges may include a convex surface configured for placement against bone. One or more holes dimensioned to receive a corresponding fastener may extend through the flange and the ridge. At least portions of the base, the flanges, and the ridges may be porous to promote bone ingrowth. The porous portions of any of the base, the flanges, and the ridges may be defined by porous geometries which may correspond to tessellated polygonal unit cells. Such unit cells may be modeled using computer-aided design software. A fastener may be placed through any one or any combination of the holes extending through the flange and the ridge to secure the implant to a patient's bone such that a head of the fastener rests below a surface of the flange opposite the ridge.

In some arrangements, the implant may be designed through the use of virtual planning, which may include the use of a computer-aided modeling system that receives radiological image data (X-Ray, MRI, CT, etc.) taken of a patient. During the virtual planning, such a modeling system may allow a user, such as a surgeon, to add or remove any virtual flange of a virtual implant, manipulate a position or orientation of any virtual flange of the virtual implant, alter the dimensions of any virtual flange of the virtual implant. In this manner, any of the quantity, the position, the orientation, and the shape of the flanges including any ridge on the flanges of the implant to be prepared may be preoperatively designed for production using any one or any combination of known additive manufacturing and computer-aided manufacturing techniques.

In some arrangements, the implant may be prepared intraoperatively by any one or any combination of a surgeon or other qualified medical professional and a robotically-controlled set of bending, trimming, and orienting tools and instruments. In some arrangements, the implant may be prepared at a remote manufacturing location using standard bending, trimming, and orienting tools. In still other arrangements, the implant may be prepared either intraoperatively or at a remote manufacturing location using a reverse-matching overhead stamping, or other electromechanical forming tool, or by using an additive manufacturing process. In some such arrangements, such tool may be an adjustable plate and, in some other arrangements, such tool may be a series of pins driven by programmable actuators. In some such arrangements, such additive manufacturing processes may be stereolithography (SLA), fused deposition modeling (FDM), continuous liquid interface production (CLIP), selective laser sintering (SLS), selective laser melting (SLM), electron beam melting (EBM), and other 3D printing technologies known to those of skill in the art.

In some arrangements, the implant may be made of certain metals such as but not limited to any one or any combination of titanium and its alloys, stainless steel and its alloys, magnesium and its alloys, cobalt and its alloys including a cobalt chrome alloy, nickel and its alloys, silver, tantalum, and niobium. In some arrangements, the implant may be made of certain plastics and other polymers such as but not limited to any one or any combination of polyethylene (PE) and variations thereof, polyetheretherketone (PEEK), polyetherketone (PEK), acrylonitrile butadiene styrene (ABS), silicone, and cross-linked polymers. In some arrangements, the implant may be made of certain other materials such as but not limited to bioabsorbable glass, ceramics, and biological active materials including collagen/cell matrices. In some arrangements, the implant may be made of a combination of any of these metals, polymers, and other materials.

In accordance with another aspect, an implant may include a base, a flange, and a ridge. The flange may extend from the base. At least a first portion of the flange may define a plane. A ridge may extend from the first portion of the flange in a direction transverse to the plane. A hole may extend through the flange and the ridge.

In some arrangements, the hole may be threaded. In some arrangements, the hole may be in the shape of an oval, and in some such arrangements, the hole may be in the shape of a circle.

In some arrangements, the base may include opposing convex and concave surfaces. In some such arrangements, the convex surface may be configured for placement against bone and the concave surface may define a bearing surface.

In some arrangements, the ridge may include a convex surface. In some such arrangements, the base may include a convex surface. In some such arrangements, the convex surfaces of the base and the ridge may be configured for placement against bone.

In some arrangements, at least a portion of the ridge may be porous. In some such arrangements, the ridge may be defined by porous geometries. In some such arrangements, the porous geometries may correspond to polygonal unit cells defining at least a portion of a virtual model of the implant. In some such arrangements, the polygonal unit cells may be tessellated within the virtual model of the implant.

In some arrangements, the base of the implant may be in the form of an acetabular cup shell. In some such arrangements, the base may define a dome and a circumferential lip within a plane opposite a tip of the dome. In some such arrangements, the flange may attach to the base within the plane and may extend from the base in a direction away from the plane.

In some arrangements, the implant may include either or both of at least one additional flange and at least one additional ridge. In any such arrangements, any one or any combination of the quantity, location, and shape of the flanges may be based on patient-specific information. Such patient-specific information may be obtained by a CT scan or other use of x-rays or by magnetic resonance imaging (MRI) or other known imaging device. In some arrangements, any of the ridges may extend from any of the flanges, including from the same flange, in different directions.

In some arrangements, the hole may be dimensioned to receive a corresponding fastener that may extend through the flange and the ridge.

In some arrangements, the flange may be in the form of a flat plate having opposing flat surfaces. In some such arrangements, the ridge may extend from one of the flat surfaces of the flange.

In some arrangements, the implant may be part of a system that may also include a fastener extending through the ridge of the implant. In some such arrangements, the ridge may include opposing convex and concave surfaces. In some such arrangements, the fastener may include a head and a shank in which the head of the fastener may be received against the concave surface of the ridge. In some such arrangements, the head of the fastener may reside completely within the combination of the ridge and the flange.

In some arrangements of the system of the implant and the fastener, the system may further include at least one additional ridge and at least one additional fastener. Any of the ridges may extend from the flange. Each additional fastener may extend through a respective ridge of any such ridges of the implant. In some such arrangements, at least two of the fasteners may extend through their respective ridges in different directions.

In accordance with another aspect, an implant may be placed into bone by a process. In such process, a base of an implant may be secured to a main complementary contact surface of bone. In such process, a ridge extending outwardly from a face of a flange of the implant may be secured to a secondary complementary contact surface of bone spaced from the main complementary contact surface.

In some arrangements, bone may be removed from a patient to form the secondary complementary contact surface. In some arrangements, bone may be removed from a patient to form the main complementary contact surface. In some such arrangements, bone may be removed from the patient such that the main complementary contact surface and the at least one second complementary contact surface are concave. In some such arrangements, bone may be removed from the patient in a flange region of bone extending from the main complementary contact surface to the secondary complementary contact surface, and in some instances, beyond the secondary complementary surface. In such arrangements, the flange region may correspond to a profile of the flange such that an entire perimeter of the flange may be inserted into the flange region when the base of the implant is secured to the main complementary contact surface of bone and the ridge is secured to the secondary complementary contact surface of bone. In some such arrangements, bone may be removed in the flange region to the depth of the flange or to depths less than or greater than the depth of the flange in which additional bone may be removed for receipt of the ridge than in other arrangements in which bone is not removed from the flange region. In such arrangements in which bone is removed to the depth of the flange, the flange may be received in the flange region such that a face of the flange opposite the face of the flange from which the ridge extends, i.e., an outwardly facing surface of the flange when the flange is seated in the intermediate region of bone, sits flush with the adjacent bone. In such arrangements, the adjacent bone around the flange may be resected, unresected, or partially resected and partially unresected. In any such arrangements, the bone may be removed by a robotically-controlled cutting tool.

In some arrangements, the bone may be a pelvic bone of a patient and the implant may include an acetabular cup shell. In some such arrangements, the implant may further include an acetabular insert having a convex outer surface conforming to and received within a concave surface of the acetabular cup shell. In some such arrangements, the implant may further include a bearing having a convex outer surface conforming to and received within a concave surface of the acetabular insert. In some such arrangements, the bearing may include a bearing surface for receiving and conforming or substantially conforming to a femoral head of a femur of the patient or to a femoral head of a femoral prosthesis for the patient.

In some arrangements, the secondary complementary contact surface may be defined by a curvature of a resection in the bone. In some such arrangements, the flange may be shaped intraoperatively to conform to the secondary complementary contact surface. In some such arrangements, the flange may be shaped after exposing the bone. In some arrangements, the main complementary contact surface may be defined by a curvature of another resection in the bone.

In some arrangements, the flange may be shaped such that when the ridge is secured to the secondary complementary contact surface, the ridge extends into a dense region of bone.

In some arrangements, the flange may be shaped at a remote manufacturing facility. In some arrangements, the flange may be stamped with a programmable stamping tool to bend the flange. In some such arrangements, the flange may be stamped by actuating a series of pins acting in tandem to bend the flange.

In some arrangements, the implant may be made of certain metals such as but not limited to any one or any combination of titanium and its alloys, stainless steel and its alloys, magnesium and its alloys, cobalt and its alloys including a cobalt chrome alloy, nickel and its alloys, silver, tantalum, and niobium. In some arrangements, the implant may be made of certain plastics and other polymers such as but not limited to any one or any combination of polyethylene (PE) and variations thereof, polyetheretherketone (PEEK), polyetherketone (PEK), acrylonitrile butadiene styrene (ABS), silicone, and cross-linked polymers. In some arrangements, the implant may be made of certain other materials such as but not limited to bioabsorbable glass, ceramics, and biological active materials including collagen/cell matrices. In some arrangements, the implant may be made of a combination of any of these metals, polymers, and other materials.

In accordance with another aspect, an implant may include an acetabular cup shell, a flange, and a ridge. The acetabular cup shell may include opposing convex and concave base surfaces. The convex base surface may be configured for placement against bone and the concave base surface may define a bearing surface. The flange may extend from the acetabular cup shell. The ridge may extend from the flange. Any one or any combination of the quantity, location, and shape of the flange may be based on patient-specific information such as described previously herein. The ridge may include a convex ridge surface that may be configured for placement against bone. At least one hole may be dimensioned to receive a corresponding fastener that may extend through the flange and the ridge. At least a portion of the ridge may be porous. In some arrangements, at least a portion of the flange may be porous. In some arrangements, at least a portion of the acetabular cup shell may be porous.

BRIEF DESCRIPTION OF THE DRAWINGS

A more complete appreciation of the subject matter of the present invention and the various advantages thereof can be realized by reference to the following detailed description, in which reference is made to the following accompanying drawings.

DETAILED DESCRIPTION

Figure 1A:
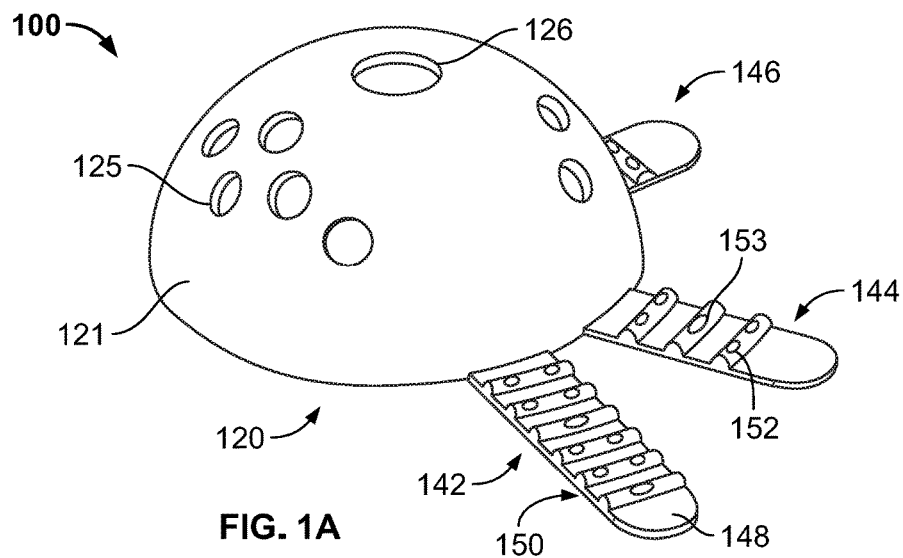
FIGS. 1A and 1B are perspective and plan views of an implant in accordance with an embodiment.
Figure 1B:
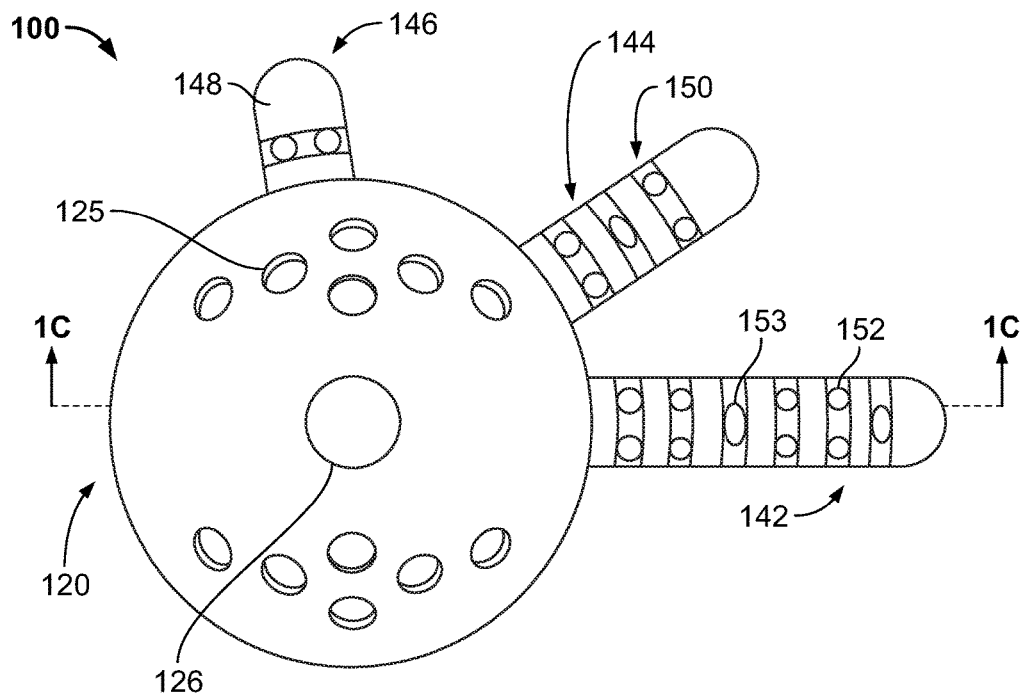
Figure 1C:
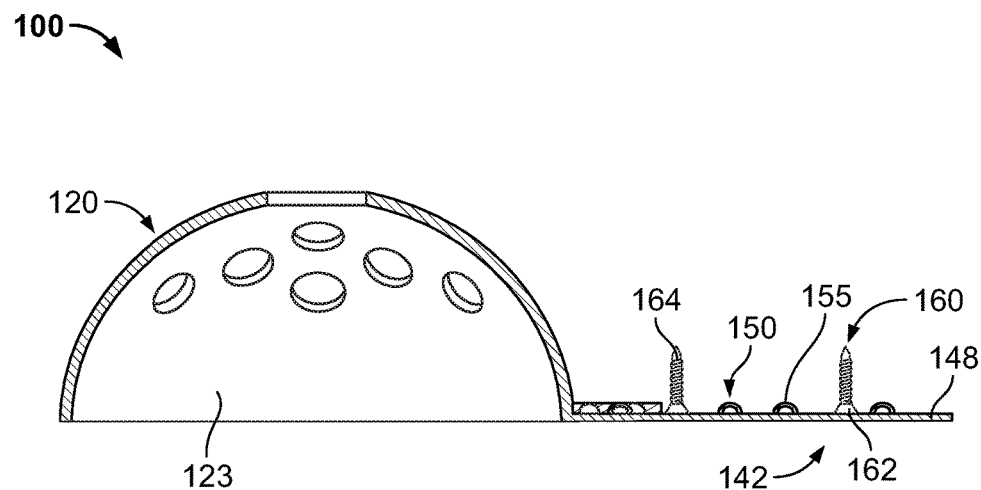
FIG. 1C is a cross-sectional view along line 1C-1C of the implant shown in FIG. 1B along with a set of fasteners positioned in the implant in accordance with another embodiment.

Referring now to the drawings, as shown in FIGS. 1A-1C, implant 100 may include base 120 and a series of flanges 142, 144, 146 extending from the base. As shown, base 120 may be in the shape of a dome having upper surface 121 and lower surface 123 and may be in the form of an acetabular cup. Upper surface 121 may be convex such that the upper surface may be inserted within a concave surface of bone, such as but not limited to an acetabulum. Lower surface 123 may be concave such that the lower surface may receive another implant. In some arrangements, as shown in implant 100 preferably may be in the form of an acetabular cup shell that lower surface 123 may be configured to receive a bearing insert, which preferably may include a polyethylene or other polymeric bearing as known to those skilled in the art. In other arrangements, the implant may be an acetabular cup for direct receipt of another bone or a prosthesis that replaces the other bone, such as but not limited to a head of a femur or femoral component prosthesis.

As in the arrangement shown, base 120 may include a series of holes 125 through the base such that fasteners may be inserted through the base. As shown, base 120 may include central hole 126 for receipt of another fastener in which the central hole may be in the diametric center of the base and may be larger than the series of holes 125. The series of holes 125 and central hole 126 may be threaded such that the series of holes and the central hole may receive locking screws with threaded heads attached to threaded shanks.

As shown, flanges 142, 144, 146 may extend radially from base 120. Flanges 142, 144, 146 may include flat portions 148 and a number of evenly spaced-apart ridges 150 raised above the flat portions. As raised ridges 150 provide the flanges with additional surface area, the ridges may serve to enhance contact with mating bone. Ridges 150 may be elongated and may extend across a longitudinal axis of flanges 142, 144, 146. As shown, ridges 150 may extend across the entire width of flanges 142, 144, 146. As in this example, flange 142 may be longer than flange 144 which may be longer than flange 146 based on optimal bone engagement locations for a patient receiving implant 100. On any of flanges 142, 144, 146, holes 152 or slots 153 may extend through ridges 150.

Ridges 150 may be porous throughout or at least at their exposed surfaces to allow for bone ingrowth and thus better engagement with bone. As one option, as in the example shown, the exposed bone-side surface of the entirety of implant 100 is porous. The porosity of the ridges preferably may be, but is not limited to being, in the range from and including 60% to 80%. To provide for this porosity, ridges 150 or, in some arrangements, the entirety of any of flanges 142, 144, 146 or even the entirety of implant 100, may be formed using either or both of a computer-aided manufacturing process, such as but not limited to a computer numerically controlled (CNC) milling machine, and an additive manufacturing process, such as but not limited to any of the additive manufacturing processes described previously herein including selective laser sintering (SLS), selective laser melting (SLM), and electron beam melting (EBM) processes, as more fully described in any of U.S. Pat. Nos. 7,537,664; 8,728,387; and 9,180,010 ("the '010 Patent") as well as U.S. Patent Application Publication No. 2006/0147332 A1, each of which is hereby incorporated by reference in their entireties herein. In one example, ridges 150 may be defined by porous geometries which may correspond to a tessellated set of polygonal unit cells or may be randomized as further described in the '010 patent.

As shown in FIG. 1C, fasteners 160 may be inserted through any of holes 152 and slots 153. Fasteners 160 may include head 162 and shank 164 extending from the head. In this manner, as further shown, upon insertion of fastener 160 into ridge 150, head 162 may be seated against concave ridge surface 155 and shank 164 may extend through the ridge surface. In this manner, fasteners 160 may be inserted into flanges 142, 144, 146 without protruding from the side of the flange opposite ridges 150.

Figure 1D:
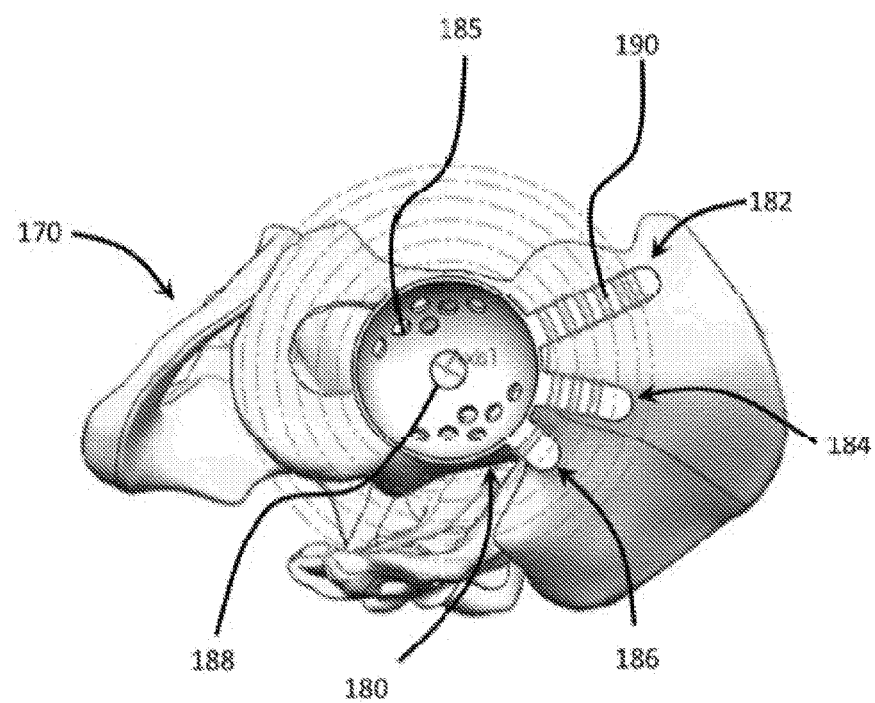
FIG. 1D is a virtual image of a plan view of a virtual implant corresponding to the implant of FIG. 1A and a virtual bone in accordance with another embodiment.

Referring to FIG. 1D, implant 100 may be prepared as a patient-specific implant. In preparing such an implant, the patient's anatomy around at least the region for treatment may be scanned, such as by a CT scan or other use of x-rays or by magnetic resonance imaging (MRI) or other known imaging device. The scanned image may then be converted to virtual patient-specific bone image 170, such as the pelvic image shown in FIG. 1D, on a monitor or other display using computer-aided modeling and segmentation software. Such software may be but is not limited to Imorphics™, which is wholly owned by Imorphics Limited, a subsidiary of Stryker® Corporation, Stryker® Orthopaedics Modeling and Analytics (SOMA) by Stryker® Corporation, GeoMagic® by 3D Systems, Inc., and 3D Slicer software developed by the Massachusetts Institute of Technology. A manual segmentation or an automatic segmentation process, such as either of the processes described in U.S. Pat. No. 7,584,080 and U.S. Patent Application Publication No. 2011/0194739 A1, which are hereby incorporated by reference in their entireties herein, may be used. Virtual implant 180, which may be but is not limited to being a standard sized implant based on a patient database such as but not limited to the SOMA System, may be overlaid onto virtual bone image 170. Although virtual implant 180 may be a standard implant, the virtual implant may generally correspond to physical implant 100 that is to be produced and used during a surgical procedure inserting implant 100 into a patient.

As shown, virtual implant 180 may be placed into appropriate position onto virtual bone image 170 such that a user of the SOMA or other similar computer-aided modeling system, e.g., a surgeon, may view the implant and bone in the direction of insertion of the implant during a surgical procedure, in this example the spherical center of the acetabulum. As such, the user may orient the position of virtual implant 180 relative to virtual bone image 170 to allow the user to determine appropriate sizes, relative positions, and relative orientations, of virtual flanges 182, 184, 186 corresponding to flanges 142, 144, 146, respectively, of implant 100, and in some arrangements, virtual holes 185 and central hole 188 corresponding to the series of holes 125 and central hole 126 of implant 100, respectively. In this manner, the user can size and orient virtual implant 180 such that implant 100 may be prepared for later fastening to denser regions of bones of the patient's anatomy.

As in the example shown, virtual implant 180 may include virtual ridges 190 extending from virtual flanges 182, 184, 186 (a profile of virtual ridges 190 being shown in FIG. 1D on a side of flanges 182, 184, 186 opposite virtual ridges 190 of virtual implant 180) and corresponding to ridges 150 of implant 100. Virtual ridges 190 may be positioned by the user relative to the bone in order to align with denser regions of bone, in this example on regions of the ilium of a patient. Once the virtual ridges are appropriately positioned, the positions may be stored for later use in preparing the bone as further described herein. The size, position and orientation of virtual ridges 190 may be planned prior to the manufacture of implant 100. During the planning of virtual ridges 190, image information relating to the density of available bone stock may be obtained and analyzed. It is preferable for virtual ridges 190 to be placed for contact and interface with sufficiently dense virtual bone stock whether the corresponding bone of a patient is resected to receive ridges 150 corresponding to the virtual ridges prior to implantation of implant 100 or ridges 150 are press-fit into the bone.

Figure 2A:
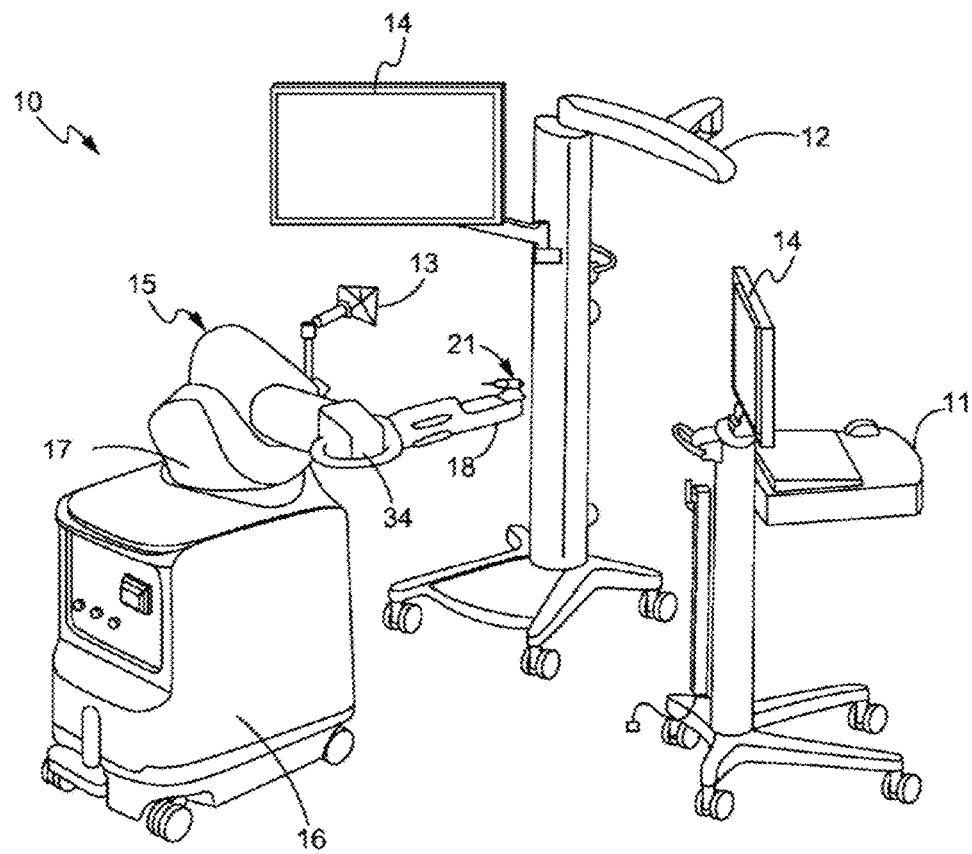
FIG. 2A is a perspective view of a surgical robotic system for use in accordance with another embodiment.
Figure 2B:
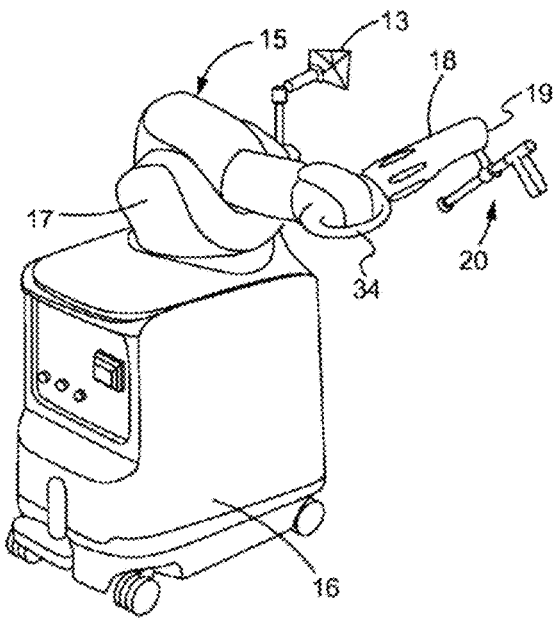
FIG. 2B is a perspective view of a base control unit and robotic arm of the surgical robotic system shown in FIG. 2A along with a surgical tool for use in accordance with another embodiment.

Referring to FIGS. 2A and 2B, surgical robotic system 10 may be used for various procedures, including, but not limited to, joint replacements, such as hip replacements, as further described in U.S. Pat. Nos. 9,161,760 and 9,275,192 hereby incorporated by reference in their entireties herein. Surgical system 10 may be the RIO® Robotic Arm Interactive Orthopedic System manufactured by MAKO Surgical Corp. of Fort Lauderdale, Fla., USA. As shown, surgical system 10 may include computer-assisted navigation system 11, tracking devices 12, 13, one or more displays 14, and robotic arm 15 pivotally mounted to base control unit 16 which may include various control components and a controller (not shown; typically housed in the base control unit 16). Robotic arm 15 may include base portion 17 and articulating arm 18. Arm 18 may include distal end 19 which may be pivotally coupled to, among other tools, either of surgical drilling tool 21 shown in FIG. 2A and milling tool 20 shown in FIG. 2B having a ball burr for either or both of drilling and sculpting of bone.

Robotic arm 15 and the controller of base control unit 16 may form a force system configured to provide control or guidance to a surgeon during manipulation of surgical tool 20, 21. The force system may be configured to provide at least some force to surgical tool 20, 21 via articulating arm 18, and the controller may be programmed to generate control signals for controlling the force system. In some arrangements, the force system may include actuators and a back-driveable transmission that provide haptic (or force) feedback to constrain or inhibit the surgeon from manually moving the surgical tool beyond predefined virtual boundaries defined by haptic objects as described, for example, in U.S. Pat. No. 8,010,180 and/or U.S. Patent Application Publication No. 2012/0109150 A1, each of which is hereby incorporated by reference herein in its entirety.

Surgical system 10 may include tracking devices 12, 13 configured to track the relative locations of surgical tool 20, 21 coupled to articulated arm 18 and the patient's anatomy. Surgical tool 20, 21 may be tracked directly by tracking devices 12, 13, which may define an optical, mechanical, electromagnetic, or other known tracking system. Alternatively, the pose (i.e., position and orientation) of surgical tool 20, 21 may be determined by tracking the location of base 16 and calculating such pose based on joint encoder data from joints of robotic arm 15 and a known geometric relationship between surgical tool 20, 21 and robotic arm 15. In particular, tracking devices 12, 13 may track or otherwise enable determination of the position of surgical tool 20, 21 and the patient's anatomy such that navigation system 11 knows the relative relationship between tool 20, 21 and the patient's anatomy (not shown).

In operation, a user (e.g., a surgeon) may manually move robotic arm 15 to manipulate surgical tool 20, 21 to perform a surgical task on the patient, such as bone cutting or implant installation. As the surgeon manipulates tool 20, 21, tracking devices 12, 13 may track the location of surgical tool 20, 21 and robotic arm 15 and haptic (or force) feedback may be provided to limit the surgeon's ability to move tool 20, 21 beyond a predefined virtual boundary that is registered (or mapped) to the patient's anatomy. In this manner, highly accurate and repeatable bone cuts and/or implant placement may result. Robotic arm 15 may operate in a passive manner and provide haptic feedback when the surgeon attempts to move the surgical tool beyond the virtual boundary. The haptic feedback may be generated by one or more actuators (e.g., rods attached to motors) in robotic arm 15 and may be but is not limited to being transmitted to the surgeon via a flexible transmission, such as a cable drive transmission. When robotic arm 15 is not providing haptic feedback, robotic arm 15 may be freely moveable by the surgeon and preferably may include a virtual brake that can be activated as desired by the surgeon. During a surgical procedure, navigation system 11 may display images related to the surgical procedure on any of displays 14.

Once the design of virtual implant 180 is finalized, implant 100 may be prepared. As described previously herein, implant 100 may be prepared entirely through the manufacturing processes described previously herein, preferably using an additive manufacturing process. Alternatively, implant 100 may be prepared from a standard implant. In one example, a surgeon or other qualified medical professional may bend and trim implant 100 in the same manner that such implants are currently modified during surgical procedures. In another example, surgical system 10 may be fitted with special instruments, which may be but are not limited to being vise grips and clamps, directly attached to robotic arm 15 of surgical system 10, in place of surgical tools 20, 21. In this example, the relative position and orientation of predetermined data of a standard implant held by surgical system 10 and of the special instruments may be tracked to facilitate any of precise bending, trimming, and orienting of the standard implant intraoperatively, i.e., during a surgical procedure. In this manner, implant 100 may be substantially identical to virtual implant 180. In yet another example, implant 100 may be prepared at a remote manufacturing location using standard bending and trimming tools. Once prepared, implant 100 may be sterile packaged and shipped in final form to the hospital at which the implantation of implant 100 is to be performed, avoiding the need for any additional instruments, e.g., plastic printed cutting guides. In still another example, implant 100 may be shaped at a remote manufacturing location or intraoperatively using special adjustable tooling. Such special tooling may include a reverse-matching reconfigurable overhead plate for stamping both sides of flanges 142, 144, 146 of a standard implant into implant 100 in order to match virtual implant 180. Alternatively, such special tooling may be a programmable pin-pressing device which has a series of pins that may be actuated to press a standard implant simultaneously at multiple locations in order to deflect the standard implant into implant 100 matching virtual implant 180.

With reference to FIGS. 1D, 2A, and 2B, surgical robotic system 10 may be used to prepare bone to receive implant 100. In this example, one or more virtual boundaries corresponding to the pre-planned locations on the bone for receipt of fasteners may be set to provide haptic feedback to the surgeon should robotic arm 15 be manipulated to cause surgical tool 20, 21 to extend beyond the boundaries. After exposing bone, the surgeon may manipulate surgical tool 20, 21, as described previously herein, to any of mill cavities within the bone for receipt of ridges 150 of implant 100 and drill holes for receipt of fasteners 160 and any fasteners to be received through the series of holes 125 and central hole 126 of base 120 of the implant. Once the appropriate holes and cavities have been formed, implant 100 may be inserted into position such that the pre-drilled holes and cavities align with the corresponding series of holes 125, central hole 126, holes 152, and slots 153, as applicable. Appropriate fasteners then may be threaded into implant 100 and the patient's bone to secure the implant. During the planning phase, as described above with respect to the virtual ridges 190, the size, position and orientation of fasteners 160 may also be determined by analyzing the available bone stock. It is preferable that the fastener may be secured to bone that will maintain the position of implant 100. Methods of planning the size, position and orientation of fasteners 160 with respect to one or more implant holes, such as holes 125, central hole 126, holes 152, and slots 153 of implant 100, for example, are disclosed in U.S. Ser. No. 14/789,462 titled "Implant Placement Planning," the disclosure of which is hereby incorporated by reference herein in its entirety.

Figure 3A:
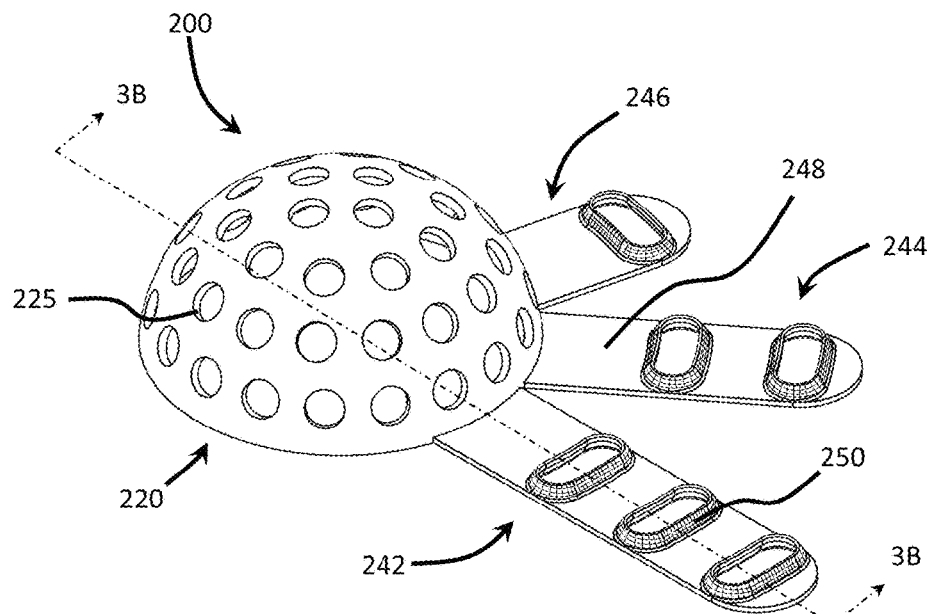
FIG. 3A is a perspective view of an implant in accordance with another embodiment.
Figure 3B:
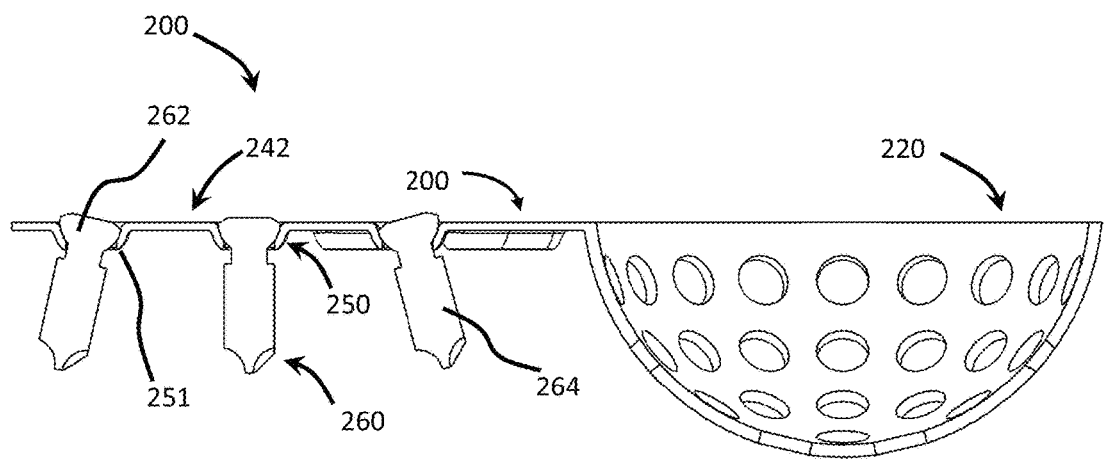
FIG. 3B is a cross-sectional view along line 3B-3B of the implant shown in FIG. 3A along with a set of fasteners positioned in the implant in accordance with another embodiment.

Referring to FIGS. 3A and 3B, implant 200 may include base 220 and a series of flanges 242, 244, 246 extending from the base. Like implant 100, implant 200 may be in the form of an acetabular cup. As in the example shown, base 220 may include a series of substantially equally sized holes 225 that may be evenly spaced apart about the entire surface of the base. Flanges 242, 244, 246 may be substantially similar to flanges 142, 144, 146 of implant 100 with the notable exception that flanges 242, 244, 246 may include evenly spaced apart ridges 250 that may extend from flat portions 248. As shown, flange 242 may include three ridges 250, flange 244 may include two ridges, and flange 246 may include one ridge 250. As further shown, each ridge 250 may be longitudinally aligned such that a longest dimension of each ridge extends nearly the width of the respective flange 242, 244, 246 that is perpendicular to the length of the flange measured in a direction radial to base 220. Each ridge 250 may define a respective central axis that extends at an angle to the surface of flat portion 248 from which the ridge extends that is different than the angle that the respective central axis of another ridge extends from the flat portion of any of the flanges, including of the same flange. In this manner, as shown in FIG. 3B, shank 264 of fasteners 260 may be inserted through holes 251 defined by ridges 250 such that head 262 of each of the fasteners rests on a respective ridge 250 and such that the shank of each fastener extends from flat portion 248 of flanges 242, 244, 246 in a different direction than at least some of the other fasteners extend from the flat portion through which those fasteners extend.

Figure 3C:
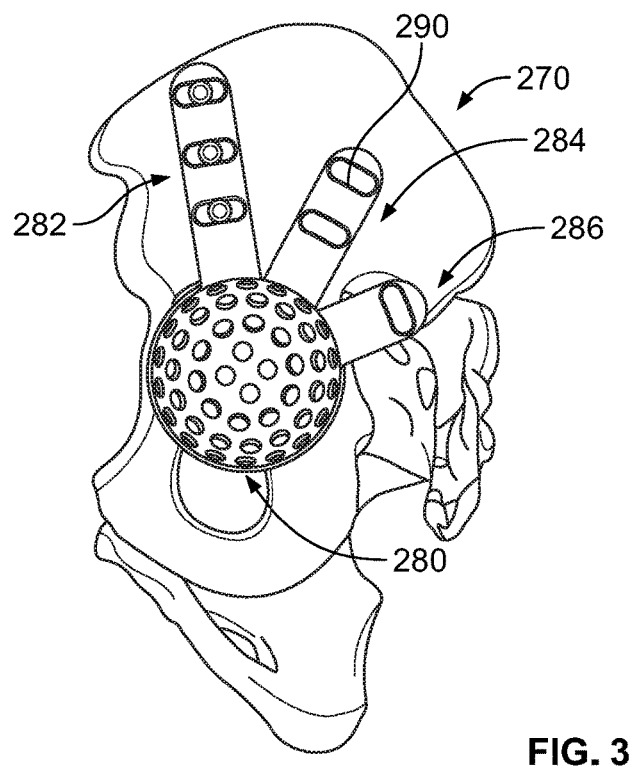
FIG. 3C is a virtual image of a plan view of a virtual implant corresponding to the implant of FIG. 3A and a virtual bone in accordance with another embodiment.

Like ridges 150 of implant 100, ridges 250 may be porous throughout or at least at their exposed surfaces to allow for bone ingrowth and thus better engagement with bone. To provide for this porosity, ridges 250 or, in some arrangements, the entirety of any of flanges 242, 244, 246 or even the entirety of implant 200, may be formed using an additive manufacturing process, such as those described previously herein. In the example shown, ridges 250 are porous in which the porosity is formed by polygonal porous geometries corresponding to computer-modeled polygonal unit cells. With reference to FIG. 3C, in the same manner in which implant 100 may be prepared, implant 200 may be prepared as a patient-specific implant. In preparing implant 200, virtual implant 280 may be positioned and oriented by a user of the SOMA or a similar modeling system relative to virtual bone image 270 to allow the user to determine appropriate sizes, relative positions, and relative orientations, of virtual flanges 282, 284, 286 and virtual ridges 290 of the virtual implant corresponding to flanges 242, 244, 246 and ridges 250, respectively, of implant 200, as described previously herein with respect to the preparation of implant 100 using virtual implant 180.

Figure 4A:
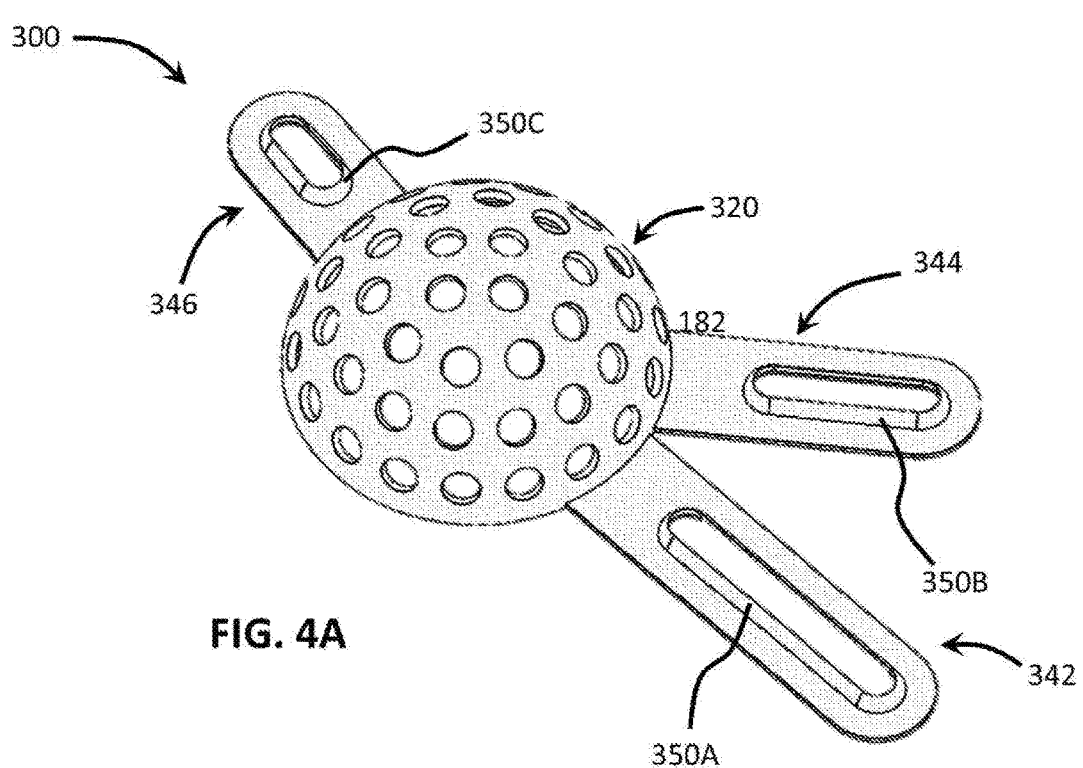
FIG. 4A is a perspective view of an implant in accordance with another embodiment.
Figures 4B, 4C:
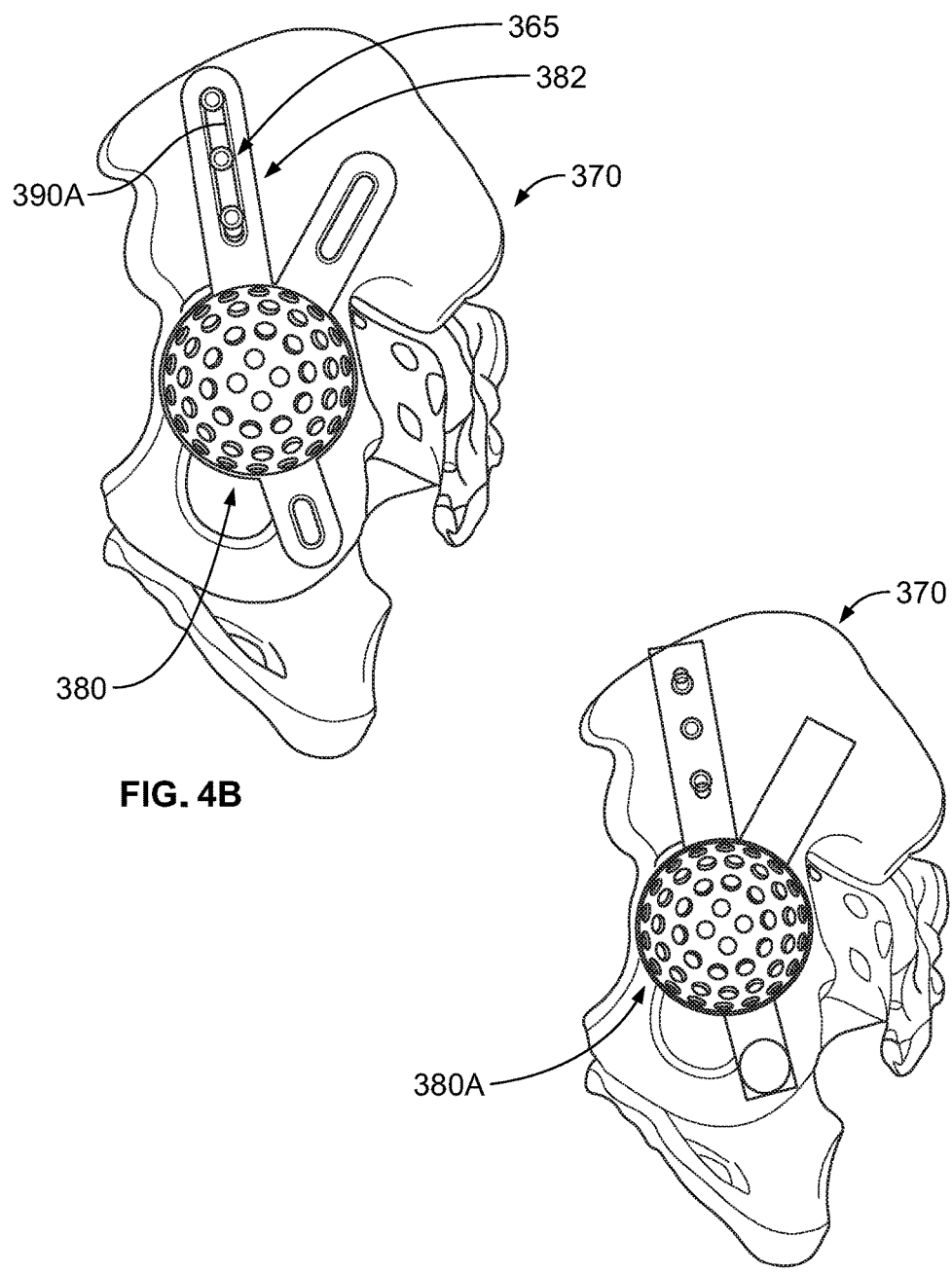
FIG. 4B is a virtual image of a plan view of a virtual implant corresponding to the implant of FIG. 4A and a virtual bone in accordance with another embodiment.
FIG. 4C is a virtual image of a plan view of an in-process virtual implant and the virtual bone of FIG. 4B.

Referring now to FIGS. 4A-4C, implant 300 may be substantially similar to implant 200 with the notable exception that implant 300 may include base 320 and flanges 342, 344, 346 in place of base 220 and flanges 242, 244, 246, respectively. Flanges 342, 344, 346 of implant 300 may be set at angles relative to each other that are different than the relative angles of flanges 242, 244, 246 of implant 200. As demonstrated by virtual implant 380 as shown in FIG. 4C, flanges 342, 344 may extend from base 320 such that longitudinal axes defined by flanges 342, 344 extend at an angle of approximately 38 degrees from each other, and flanges 342, 346 may extend from base 320 such that longitudinal axes defined by flanges 342, 346 extend at an angle of approximately 175 degrees from each other. Each of flanges 342, 344, 346 may include corresponding ridges 350A, 350B, 350C of decreasing length in place of ridges 250. A longest dimension of each of ridges 350A, 350B, 350C may extend along the respective longitudinal axes of flanges 342, 344, 346. With reference to FIG. 4B, a series of fasteners, in this example three fasteners, corresponding to virtual fasteners 365 may be inserted through ridge 350A (and in other arrangements, through any of ridges 350A, 350B, 350C) corresponding to virtual ridge 390A of virtual flange 382 of virtual implant 380 such that a virtual head of the virtual fasteners rests on the virtual ridge. As demonstrated by virtual implant 380, the fasteners corresponding to virtual fasteners 365 may be spaced apart along the ridge.

Implant 300 may be prepared in the same manner as implants 100, 200. In this example and with reference to FIGS. 4B and 4C, using the SOMA or similar imaging system, the fasteners corresponding to virtual fasteners 365 are planned by the user, using in-process virtual implant 380A placed on virtual bone 370 as shown in FIG. 4C, to be located relative to base 320 of the prepared implant such that each of the respective longitudinal axes of the fasteners intersects a respective circumference substantially coplanar with flange 342 and coaxial to a central axis of the base at respective distances of 55 mm, 75 mm, and 95 mm from the central axis of the base. These distances for fastener insertion as well as the relative angles between flanges 342, 344, 346 are determined by the user to correspond to optimal locations for the fasteners for bone engagement.

Figure 5:
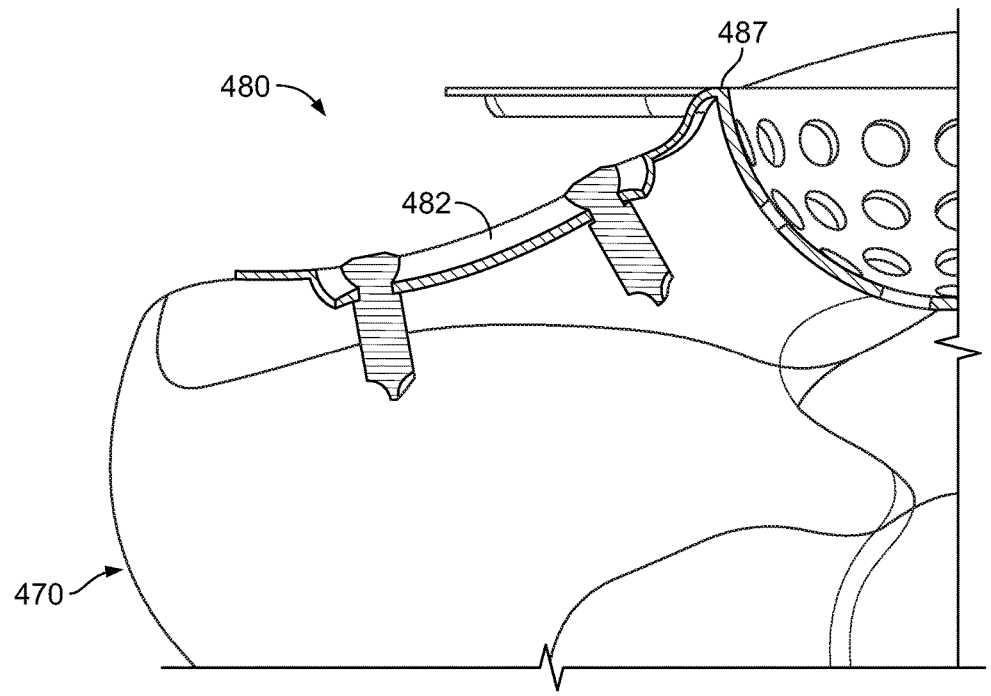
FIG. 5 is a virtual image of a cross-sectional view of a virtual implant and a virtual bone in accordance with another embodiment.

Referring to FIG. 5, an implant corresponding to virtual implant 480 may be placed on a bone corresponding to virtual bone image 470 in the same manner the virtual implant is placed on the virtual bone image. As shown, virtual implant 480 may include virtual flange 482, which may be substantially similar to virtual flange 382, that is bent away from a plane defined by virtual base lip 487 of the virtual implant. In this manner, the implant corresponding to virtual implant 480 may be prepared to include a flange bent away from a plane defined by a lip of a base of the implant, such as base 320 of implant 300.

As demonstrated by FIG. 5, bone corresponding to virtual bone image 470 may be prepared, such as by using surgical system 10 described with respect to FIGS. 2A and 2B, to receive the flange corresponding to virtual flange 482 such that the contours of the flange and of the prepared bone match as closely as possible within the geometric limitations of surgical tools 20, 21 of the surgical system.

Figure 6A:
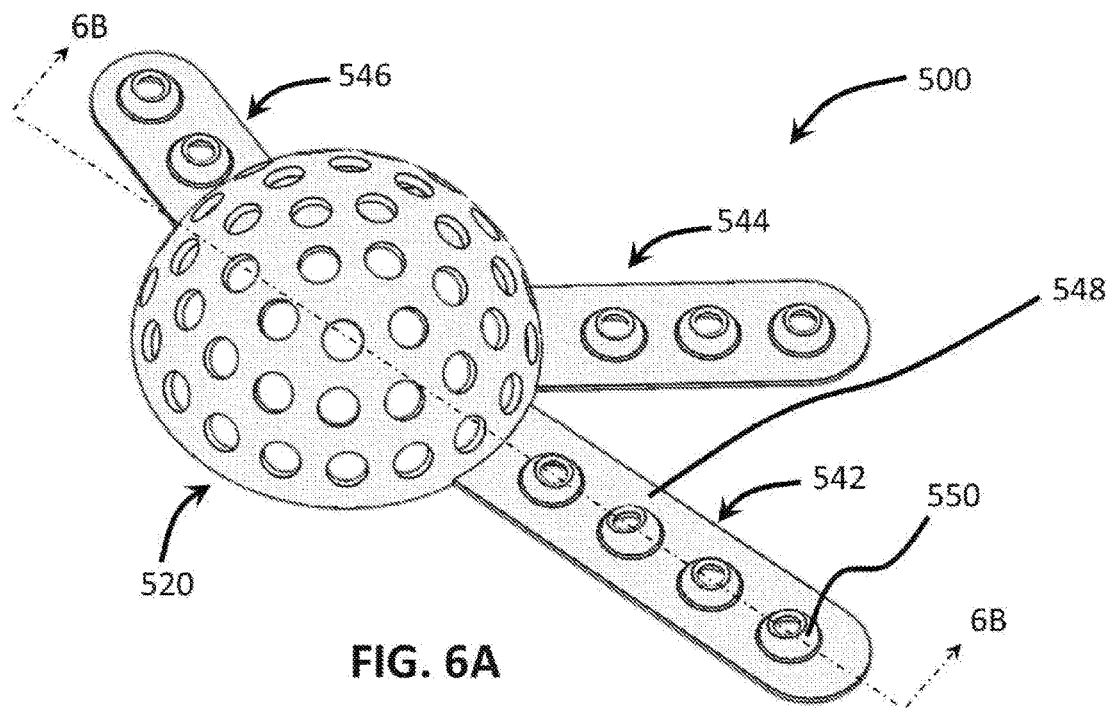
FIG. 6A is a perspective view of an implant in accordance with another embodiment.
Figure 6B:
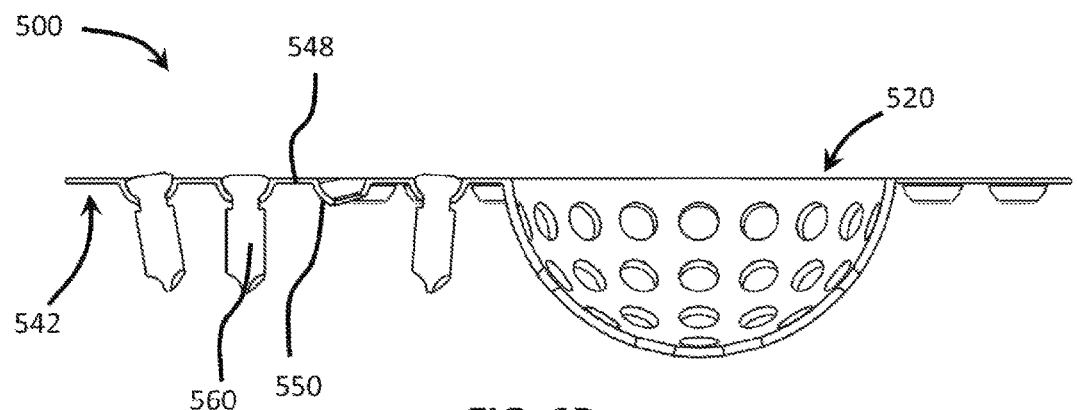
FIG. 6B is a cross-sectional view along line 6B-6B of the implant shown in FIG. 6A along with a set of fasteners in accordance with another embodiment.
Figure 6C:
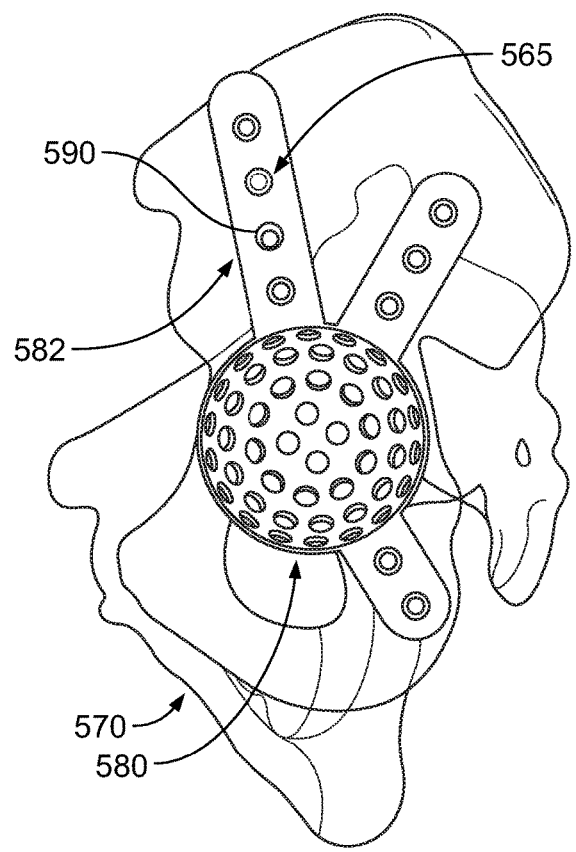
FIG. 6C is a virtual image of a plan view of a virtual implant corresponding to the implant of FIG. 6A and a virtual bone in accordance with another embodiment.

Referring now to FIGS. 6A-6C, implant 500 may be substantially similar to implant 300 with the notable exception that implant 500 may include base 520 and flanges 542, 544, 546 in place of base 320 and flanges 342, 344, 346, respectively. Flanges 542, 544, 546 of implant 500 may be set at angles relative to each other that are different than the relative angles of flanges 342, 344, 346 of implant 300. As demonstrated by virtual implant 580 placed on virtual bone 570 as shown in FIG. 6C, flanges 542, 544 may extend from base 520 such that longitudinal axes defined by flanges 542, 544 extend at an angle of approximately 42 degrees from each other, and flanges 542, 546 may extend from base 520 such that longitudinal axes defined by flanges 542, 546 extend at an angle of approximately 160 degrees from each other. Each of flanges 542, 544, 546 may include corresponding partially spherical ridges 550 in place of ridges 350A, 350B, 350C. As best shown in FIG. 6B, ridges 550 of implant 500 may be prepared such that central axes defined by the ridges may form different predetermined angles with a plane parallel to flat portion 548 of flanges 542, 544, 546. With reference to FIGS. 6B and 6C, a series of fasteners 560, in this example three fasteners, corresponding to virtual fasteners 565 may be inserted through respective ridges 550 (and, as demonstrated in FIG. 6C, through ridges 550 of other flanges 544, 546) corresponding to virtual ridges 590 of virtual flange 582 of virtual implant 580. As further shown, ridges 550, and thus fasteners inserted into the ridges, may be spaced apart substantially evenly along respective flanges 542, 544, 546.

Implant 500 may be prepared in the same manner as implants 100, 200, 300. In this example and with reference to FIGS. 6B and 6C, using the SOMA or similar imaging system, fasteners 560 corresponding to virtual fasteners 565 are planned by the user to be located relative to the base 520 of the prepared implant such that each of the respective longitudinal axes of the fasteners intersects a respective circumference substantially coplanar with flange 542 and coaxial to a central axis of the base at respective distances of 55 mm, 75 mm, and 95 mm from the central axis of the base. These distances for fastener insertion as well as the relative angles between flanges 542, 544, 546 are determined by the user to correspond to optimal locations for the fasteners for bone engagement as to a particular patient.

In some alternative arrangements, the base of the implant may include a fewer or greater number of holes than that shown in the embodiments described herein. Such holes may be unthreaded and may be configured to receive compression screws. The holes may be slots or have profiles other than circles and ovals as shown in the example of implant 100. The implant may include a fewer or greater number of flanges than that shown in the embodiments described herein. Each flange may have any of the same shape and size as the other flanges or may have any of a different shape and a different size than the other flanges.

In some alternative arrangements, the ridges may not be evenly spaced. In some alternative arrangements, at least some of the ridges may be in the form of round bosses instead of elongated ridges. Any of the holes and slots in the flanges may be positioned at different locations on the ridges than the locations shown in the example shown in FIGS. 1A and 1B, and in some alternative arrangements, at least some of the holes and slots may be positioned through the flat portions of the flanges.

It is to be understood that the disclosure set forth herein includes all possible combinations of the particular features set forth above, whether specifically disclosed herein or not. For example, where a particular feature is disclosed in the context of a particular aspect, arrangement, configuration, or embodiment, that feature can also be used, to the extent possible, in combination with and/or in the context of other particular aspects, arrangements, configurations, and embodiments of the invention, and in the invention generally.

Furthermore, although the invention disclosed herein has been described with reference to particular features, it is to be understood that these features are merely illustrative of the principles and applications of the present invention. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the claims below.

The invention claimed is:

1. An implant comprising:
a base defining a dome and a circumferential rim;
an elongated flange extending outwardly from the base, at least a first portion of the flange defining a plane and having opposing flat surfaces; and
a ridge extending from the first portion of the flange in a direction transverse to the plane and including opposing concave and convex surfaces, wherein a hole extends through the flange and the ridge and is configured for receipt of a portion of a fastener having a head and a shank, wherein the convex surface of the ridge is a bone-contacting surface, and wherein the concave surface of the ridge is configured for receipt of the head of the fastener.

2. The implant of claim 1, wherein the base includes opposing convex and concave surfaces, the convex surface configured for placement against bone and the concave surface defining a bearing surface.

3. The implant of claim 1, wherein the base includes a convex surface, and wherein the convex surfaces of the base and the ridge are configured for placement against bone.

4. The implant of claim 1, wherein at least a portion of the ridge is porous.

5. The implant of claim 4, wherein the ridge is defined by porous geometries.

6. The implant of claim 5, wherein the porous geometries correspond to polygonal unit cells.

7. The implant of claim 1, wherein the base of the implant comprises an acetabular cup shell.

8. The implant of claim 7, wherein the flange extends from the circumferential rim.

9. The implant of claim 1, further comprising at least one additional flange, and wherein any one or any combination of the quantity, location, and shape of the flanges are based on patient-specific information.

10. The implant of claim 1, wherein the ridge is a first ridge, further comprising at least one additional ridge extending from the flange, and wherein any one or any combination of the quantity, location, orientation, and shape of the ridges are based on patient-specific information.

11. The implant of claim 10, wherein the first ridge and at least one of the additional ridges extend from the flange in different directions.

12. The implant of claim 1, wherein the hole is dimensioned to receive the corresponding fastener that extends through the flange and the ridge.

13. The implant of claim 1, wherein the flange is in the form of a flat plate.

14. A system comprising:
the implant of claim 1; and
the fastener extending through the ridge of the implant.

15. The system of claim 14, wherein the head of the fastener resides completely within the combination of the ridge and the flange.

16. The system of claim 14, further comprising:
at least one additional ridge extending from the flange; and
at least one additional fastener, each additional fastener extending through a respective additional ridge of the implant, wherein at least two of the fasteners extend through their respective ridges in different directions.

17. The implant of claim 1, wherein the ridge and the flange are integral such that they form a one-piece structure.

18. An implant comprising:
an acetabular cup shell including opposing convex and concave base surfaces, the convex base surface being configured for placement against bone and the concave base surface defining a bearing surface;
an elongated flange extending outwardly from a circumferential rim of the acetabular cup shell and having opposing flat surfaces; and
a ridge monolithic with the flange extending from one of the flat surfaces of the flange, wherein any one or any combination of the quantity, location, and shape of the flange is based on patient-specific information, wherein the ridge includes a convex ridge surface configured for placement against bone, wherein at least one hole extends through the flange and the ridge and is dimensioned to receive a portion of a corresponding fastener having a head and a shank, wherein a concave surface of the ridge is configured for receipt of the head of the fastener, and wherein at least a portion of the acetabular cup shell, a portion of the flange, and a portion of the ridge are porous.

* * * * *